(12) United States Patent
Corfas et al.

(10) Patent No.: US 7,863,295 B2
(45) Date of Patent: Jan. 4, 2011

(54) TREATMENTS FOR NEUROPATHY

(75) Inventors: Gabriel Corfas, Brookline, MA (US); Joshua C. Murtie, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 164 days.

(21) Appl. No.: 12/350,751

(22) Filed: Jan. 8, 2009

(65) Prior Publication Data

US 2009/0203735 A1 Aug. 13, 2009

Related U.S. Application Data

(60) Provisional application No. 61/028,024, filed on Feb. 12, 2008.

(51) Int. Cl.
*A61K 31/4706* (2006.01)
(52) U.S. Cl. .................................... 514/313
(58) Field of Classification Search .............. None
See application file for complete search history.

(56) References Cited

U.S. PATENT DOCUMENTS 5,976,547 A * 11/1999 Archer et al. ............... 424/742
6,413,982 B1 7/2002 Yuan et al.
2004/0192728 A1 9/2004 Codd et al.

OTHER PUBLICATIONS

Tokugawa, K. et al., "XIB4035, A Novel Nonpeptidyl Small Molecule Agonist for GFRAlpha-2", Neurochemistry International, 2003, vol. 42, pp. 81-86. see abstract.

Akkina, S.K. et al., "GDNF Rescues Nonpeptidergic Unmyelinated Primary Afferents in Streptozotocin-Treated Diabetic Mice", Experimental Neurology, 2001, vol. 167, pp. 173-182.

ISA, International Search Report & Written Opinion, in PCT/US2009/032910.

* cited by examiner

*Primary Examiner*—Phyllis G. Spivack
(74) *Attorney, Agent, or Firm*—Richard Aron Osman

(57) ABSTRACT

Small fiber neuropathy is treated by topically administering to a subject in need thereof topically active quinoline compounds or pharmaceutically acceptable salts thereof under conditions effective to treat neuropathy in the subject. Glial cell-derived neurotrophic factor (GDNF) receptors are modulated with the subject active quinoline compounds, which may be formulated in topical lotions.

12 Claims, No Drawings

TREATMENTS FOR NEUROPATHY

This application claims priority to U.S. Ser. No. 61/028,024, filed Feb. 12, 2008 by the same inventors: Gabriel Corfas and Joshua C. Murtie, both of Boston, Mass.

The subject matter of this application was made with support from the National Institute for Health (NIH) Grant No. NS035884. The U.S. Government has certain rights.

FIELD OF THE INVENTION

This invention relates to methods of treating or preventing small fiber neuropathy.

BACKGROUND OF THE INVENTION

Small fiber neuropathy (SFN) is a disorder characterized by degeneration or dysfunction of small diameter unmyelinated nerve fibers in the peripheral nervous system (1, 2). Patients with SFN have sensory defects with a variety of symptoms, including loss of sensation or chronic pain. Despite its prevalence, the etiology of SFN is poorly understood and there are currently no effective treatments. Since the initial stages of SFN commonly involve degeneration of nerve terminals without loss of neuronal cell bodies (3), we wondered if delivery of therapeutic agents at the target of innervation, i.e. the skin, would be an effective non-invasive approach that could minimize the side effects commonly observed with systemic drug delivery methods.

When considering molecules that could be used in this fashion, we focused on neurotrophic factors, which have been viewed as potentially useful therapeutic agents in the treatment of peripheral neuropathies because they regulate the survival and function of peripheral nerves during development (4, 5). In addition, decreases in expression of certain trophic factors have been observed in multiple models of peripheral neuropathy (6, 7) suggesting that low levels of these factors may be involved in disease etiology. One of these trophic factors, GDNF, is necessary for proper development and survival of small diameter unmyelinated nerve fibers (5, 8). In early postnatal life, a large proportion of developing unmyelinated nerve fibers switch from dependence on nerve growth factor (NGF) to dependence on GDNF (5). This transition coincides with a gradual decrease in expression of the NGF receptor (TrkA) with a corresponding increase in the expression of GDNF family receptors by dorsal root ganglion sensory neurons (4). Based on the known roles of the GDNF pathway in peripheral nerve development and function and the pattern of expression of GDNF family ligands and receptors, we decided to test if application of GDNF receptor ligands to the skin could be used to treat SFN. To address this question, we used two mouse models of SFN arising from different pathogenic processes. In one model, progressive SFN results from disruption of non-myelinating Schwann cell (NMSC) function (6). In the other, rapid onset SFN is caused by treatment with a toxin (resiniferatoxin, RTX) that activates TRPV1 channels in c-fiber nerve terminals, inducing loss of unmyelinated fiber nerve terminals in the skin and loss of thermal nociception (9). Here we show that topical delivery of GDNF receptor ligands to affected skin areas is sufficient to prevent degeneration and maintain sensory function in both types of SFN. In addition, we demonstrate that the non-peptidyl GFRα1 agonist XIB4035 and related quinolines are capable of providing trophic support to peripheral nerves in vivo and thus are useful therapeutic agents in the treatment of SFN.

Use of N4-{7-chloro-2-[(E)-2-(2-chloro-phenyl)-vinyl]-quinolin-4-yl}-N1,N1-diethyl-pentane-1,4-diamine (XIB4035), also known as 7-chloro-2-(o-chlorostyryl)-4-[4diethylamino-1-methylbutyl]aminoquiinoline phosphate), and 2-(2-Chlorostyryl)-4-(delta-diethylamino-alpha-methyl-butylamino)-7-chloroquinazoline (CAS RN 57942-32-2; CAS 10023-54-8) has been described, e.g. Tokugawa et al., Neurochem Intnl 2003, 42, 81-86; WO01003649; and JP 2008-230974.

SUMMARY OF THE INVENTION

The invention provides methods and compositions for treating or preventing small fiber peripheral neuropathy in a subject determined to be in need thereof, and generally comprising: (a) topically administering to the subject an anti-peripheral neuropathic quinoline compound of the formula:

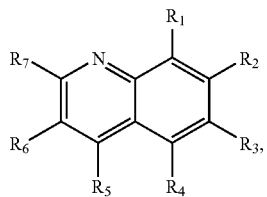

wherein $R_1$-$R_7$ are each independently H, hydroxy, halogen, substituted or unsubstituted alkyl, substituted or unsubstituted alkenyl, substituted or unsubstituted alkynyl, substituted or unsubstituted arylalkyl, substituted or unsubstituted amine, substituted or unsubstituted alkylamine, substituted or unsubstituted dialkylamine, substituted or unsubstituted alkoxy, substituted or unsubstituted aryl, substituted or unsubstituted heteroaryl, substituted or unsubstituted alkoxy, substituted or unsubstituted haloalkyl, or a pharmaceutically acceptable salt thereof, under conditions effective to treat or prevent the peripheral neuropathy in the subject.

In particular embodiments the method further comprises the antecedent step of determining that the subject is in need thereof, e.g. by detecting or diagnosing the small fiber neuropathy in the subject or patient, or that the subject is at particular risk of developing the neuropathy.

In particular embodiments, the method further comprises the subsequent step of detecting a resultant effect on the subject, such as a diminution in the severity of the neuropathy, or delayed onset of the neuropathy.

The invention encompasses all alternative combinations of particular embodiments:

$R_2$ is halogen, particularly Cl;

$R_5$ is a substituted amine, particularly optionally-substituted alkyl substituted secondary amine, particularly wherein the alkyl is substituted with a dialkylamine such as 1-methyl-3-diethylaminobutyl, 1-methyl-4-dimethylaminobutyl, 1-ethyl-4-dimethylaminobutyl, 1-ethyl-4-diethylaminobutyl, or 1-methyl-4-diethylaminobutyl:

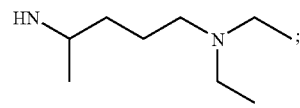

$R_7$ is a substituted alkenyl, particularly optionally-substituted phenyl substituted ethenyl, particularly such as

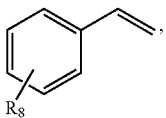

and/or
wherein $R_8$ is hydrogen or halogen, such as Cl, particularly ortho-chloro:

such as wherein the compound has formula:

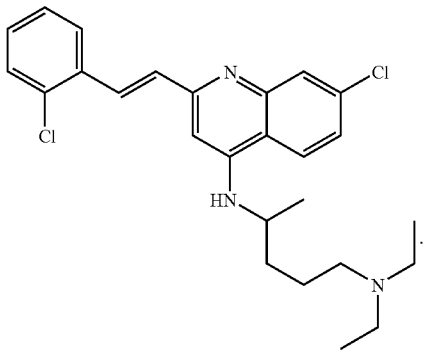

In another aspect, the invention provides methods and compositions for treating or preventing a small fiber peripheral neuropathy in a subject determined to be in need thereof, and generally comprising: topically administering to the subject an agonist of glial cell-derived neurotrophic factor (GDNF) receptor GFRα1 or GFRα2, under conditions effective to treat or prevent the peripheral neuropathy in the subject, particularly, wherein the agonist is XIB4035.

In another aspect, the invention provides a topical lotion comprising (a) a subject anti-peripheral neuropathic quinoline compound, or a pharmaceutically acceptable salt thereof; and (b) a pharmaceutically acceptable carrier formulated for topical application.

DESCRIPTION OF PARTICULAR EMBODIMENTS OF THE INVENTION

In one embodiment, the invention provides methods of treating or preventing small fiber neuropathy in a subject, particularly a human, determined to be in need thereof, the method comprising the step of (a) topically administering to the subject a compound of the formula:

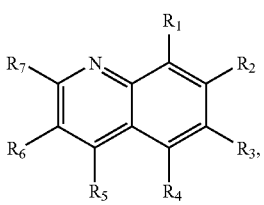

wherein $R_1$-$R_7$ are each independently H, hydroxy, halogen, substituted or unsubstituted alkyl, substituted or unsubstituted alkenyl, substituted or unsubstituted alkynyl, substituted or unsubstituted arylalkyl, substituted or unsubstituted amine, substituted or unsubstituted alkylamine, substituted or unsubstituted dialkylamine, substituted or unsubstituted alkoxy, substituted or unsubstituted aryl, substituted or unsubstituted heteroaryl, substituted or unsubstituted alkoxy, substituted or unsubstituted haloalkyl, or a pharmaceutically acceptable salts thereof under conditions effective to treat or prevent the small fiber peripheral neuropathy in the subject.

"Alkyl" as used herein refers to a saturated hydrocarbon radical which may be straight-chain or branched-chain (for example, ethyl, isopropyl, t-amyl, or 2,5-dimethylhexyl) or cyclic (for example cyclobutyl, cyclopropyl or cyclopentyl) and contains from 1 to 24 carbon atoms. This definition applies both when the term is used alone and when it is used as part of a compound term, such as "haloalkyl" and similar terms. In some embodiments, preferred alkyl groups are those containing 1 to 4 carbon atoms, which are also referred to as "lower alkyl." In some embodiments preferred alkyl groups are those containing 5 or 6 to 24 carbon atoms, which may also be referred to as "higher alkyl".

"Alkenyl," as used herein, refers to a straight or branched chain hydrocarbon containing from 2 to 24 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 24 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

"Alkoxy" refers to an alkyl radical as described above which also bears an oxygen substituent which is capable of covalent attachment to another hydrocarbon radical (such as, for example, methoxy, ethoxy and t-butoxy).

"Alkylthio" as used herein refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" or "aromatic ring moiety" refers to an aromatic substituent which may be a single ring or multiple rings which are fused together, linked covalently or linked to a common group such as an ethylene or methylene moiety. The aromatic rings may each contain heteroatoms and hence "aryl" encompasses "heteroaryl" as used herein. Representative examples of aryl include, azulenyl, indanyl, indenyl, naphthyl, phenyl, tetrahydronaphthyl, biphenyl, diphenylmethyl, 2,2-diphenyl-1-ethyl, thienyl, pyridyl and quinoxalyl. "Aryl" means substituted or unsubstituted aryl unless otherwise indicated and hence the aryl moieties may be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible.

"Halo" or "halogen," as used herein, refers to —Cl, —Br, —I or —F.

"Haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Hydroxy," as used herein, refers to an —OH group.

"Amine" or "amino" as used herein, refers to a nitrogen atom attached by single bonds to hydrogen atoms, alkyl groups, aryl groups, or a combination of these three. An organic compound that contains an amino group is called an amine. Amines are derivatives of the inorganic compound ammonia, $NH_3$. When one, two, or all three of the hydrogens in ammonia are replaced by an alkyl or aryl group, the resulting compound is known as a primary, secondary, or tertiary amine, respectively.

In certain embodiments, $R_2$ may be halogen, $R_5$ may be a substituted amine, and/or $R_7$ may be a substituted alkenyl such as

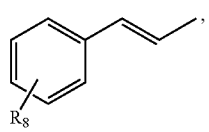

wherein $R_8$ may be H or halogen, for example, Cl.

In preferred embodiments, $R_2$ is Cl, $R_5$ is

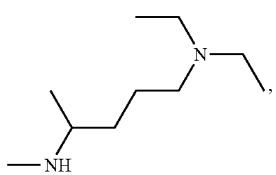

and $R_7$ is

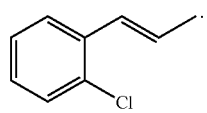

The subject topically-active, anti-peripheral neuropathic quinoline compounds are commercially available and/or readily produced using convention organic synthesis. Relevant derivitization schemes are known in the art, such as described in "Synthesis of substituted 4-(δ-diethylamino-α-methylbutylamino)-2-styrylquinolines", Berenfel'd, V. M.; Yakhontov, L. N.; Yanbukhtin, N. A.; Krasnokutskaya, D. M.; Vatsenko, S. V.; Rubtsov, M. V. Zhurnal Obshchei Khimii (1962), 32 2169-77. CODEN: ZOKHA4 ISSN: 0044-460X; "Syntheses in the isoquinoline series. Hofmann degradation of 1-phenyl-substituted 1,2,3,4-tetrahydroisoquinolines," Rheiner, A., Jr.; Brossi, A. F. Hoffmann-La Roche & Co., A.-G., Basel, Switz. Helvetica Chimica Acta (1962), 45 2590-600. CODEN: HCACAV ISSN: 0018-019X; "Synthesis and antileishmaniasis activity of 2-(2'-cholrostyryl)-4-(δ-diethylamino-α-methylbutylamino)-7-chloroquinazoline diphosphate," Yakhontov, L. N.; Zhikhareva, G. P.; Mastafanova, L. I.; Evstratova, M. I.; Pershin, G. N.; Moskalenko, N. Yu.; Pushkina, T. V.; Kutchak, S. N.; Fadeeva, N. I.; et al. VNIFI, Moscow, USSR. Khimiko-Farmatsevticheskii Zhurnal (1987), 21(1), 38-49. CODEN: KHFZAN ISSN: 0023-1134; and "Reaction products of 4-[[4-(diethylamino)-1-methylbutyl]amino]-7-chloroquinaldine with o-chlorobenzaldehyde," Uritskaya, M. Ya.; Anisimova, O. S.; Tubina, I. S.; Vinokurova, T. Yu.; Pershin, G. N.; Moskalenko, N. Yu.; Gus'kova, T. A.; Kutchak, S. N.; Stebaeva, L. F. Vses. Nauchno-Issled. Khim.-Farm. Inst., Moscow, USSR. Khimiko-Farmatsevticheskii Zhurnal (1983), 17(11), 1334-40. CODEN: KHFZAN ISSN: 0023-1134.

Anti-peripheral neuropathic activity is readily confirmed in topical formulations and the convenient animal models, as demonstrated below. The subject compounds are topically-active, antineuropathic quinolines, particularly aminoquinolines, particularly 4- and 8-aminoquinolines, particularly chloroquines (chloroquine and derivatives thereof), and include compounds of Tables 1-3:

TABLE 1

Exemplary anti-peripheral neuropathic compounds of the invention are shown in Tables 1 and 2 below:

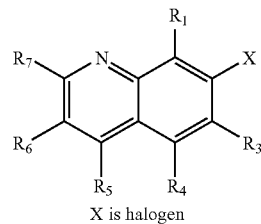

X is halogen

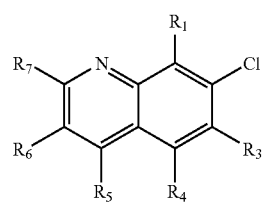

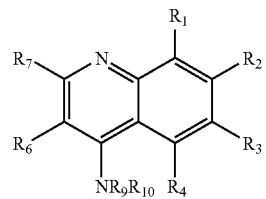

R9-R10 are defined the same as R1-R7, supra.

TABLE 1-continued
Exemplary anti-peripheral neuropathic compounds of the invention are shown in Tables 1 and 2 below:
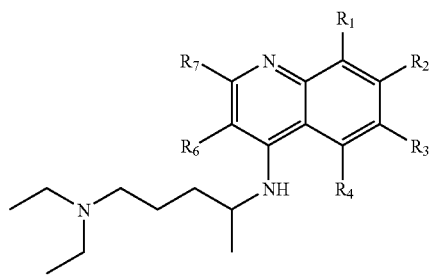
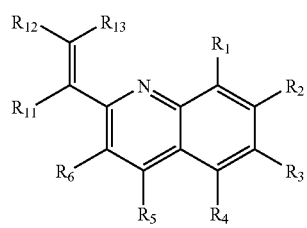
R11-R13 are defined the same as R1-R7, supra.
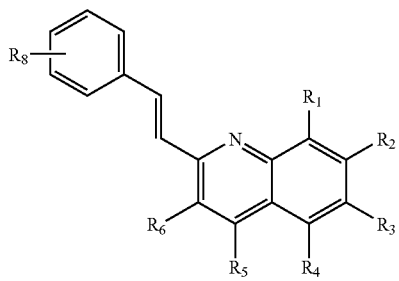
R8 may be H or halogen.
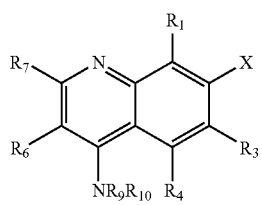
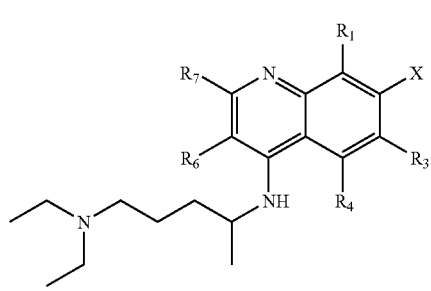
TABLE 1-continued
Exemplary anti-peripheral neuropathic compounds of the invention are shown in Tables 1 and 2 below:
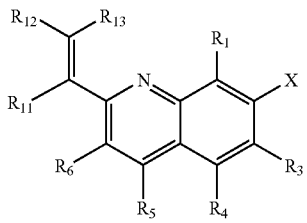
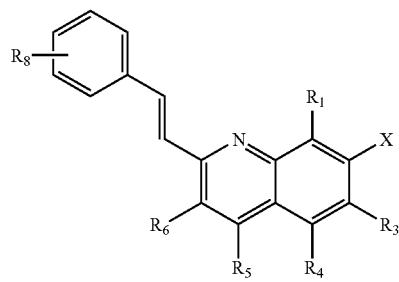
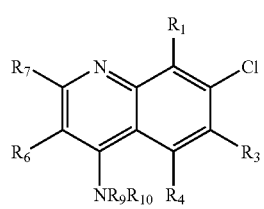
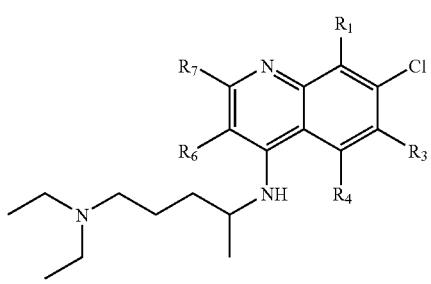
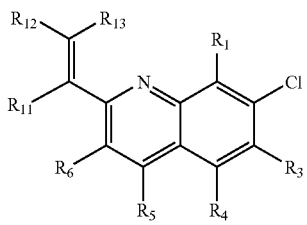
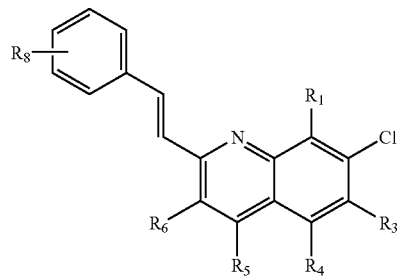

TABLE 1-continued
Exemplary anti-peripheral neuropathic compounds of the invention are shown in Tables 1 and 2 below:
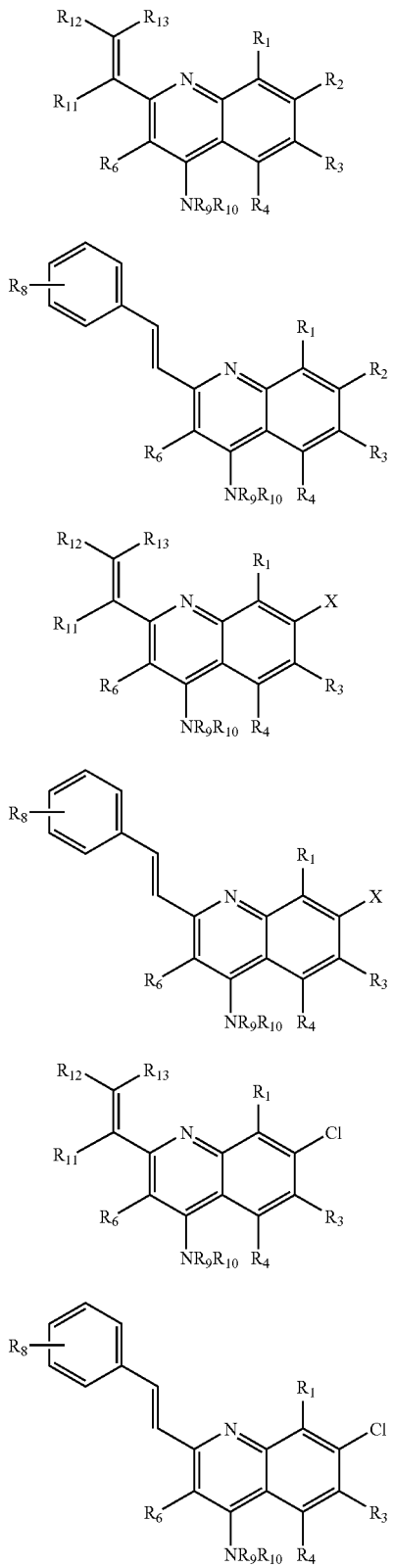
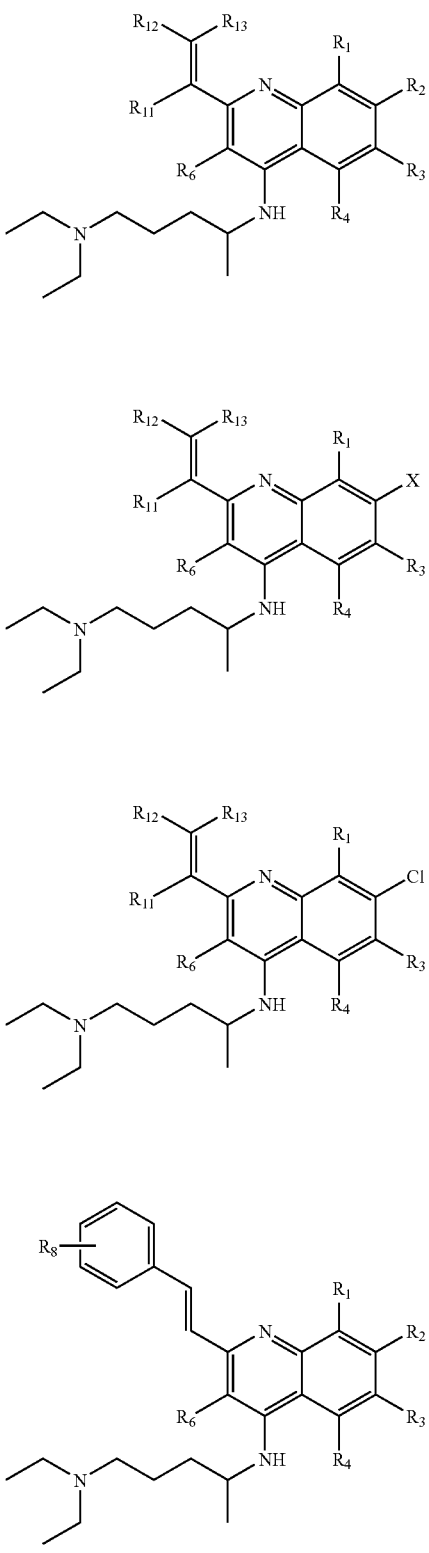

TABLE 1-continued
Exemplary anti-peripheral neuropathic compounds of the invention are shown in Tables 1 and 2 below:
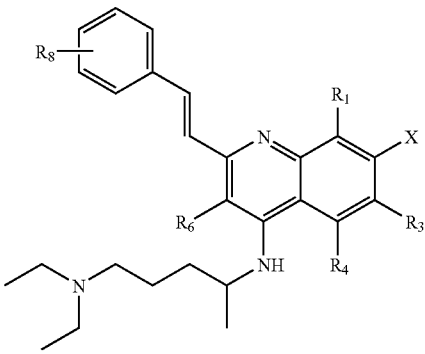
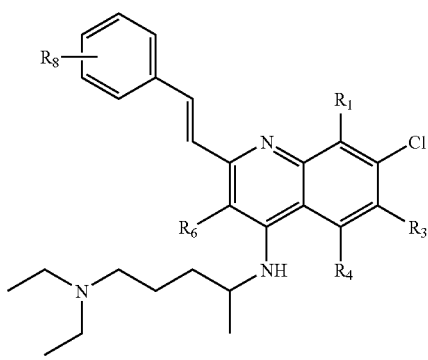
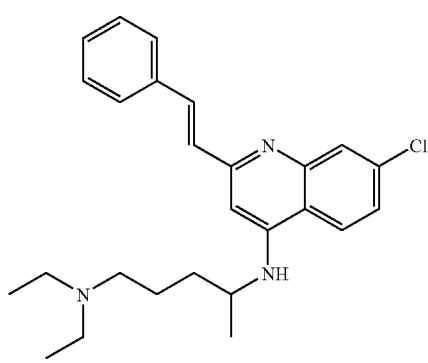
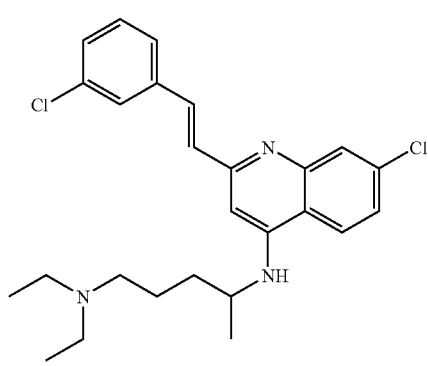
TABLE 1-continued
Exemplary anti-peripheral neuropathic compounds of the invention are shown in Tables 1 and 2 below:
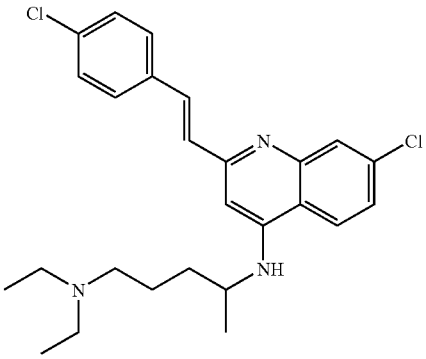
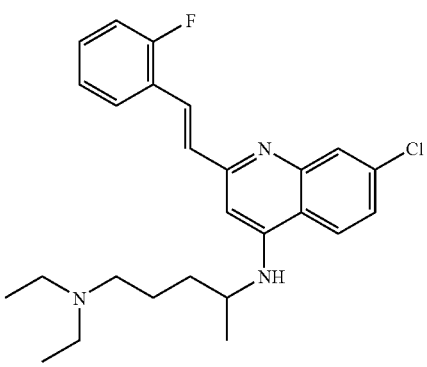
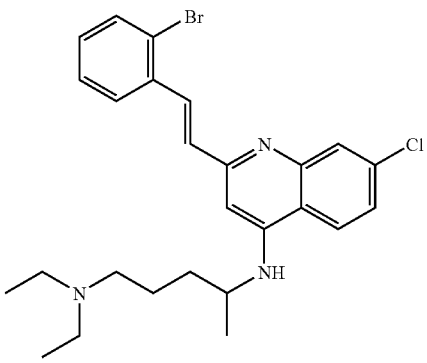
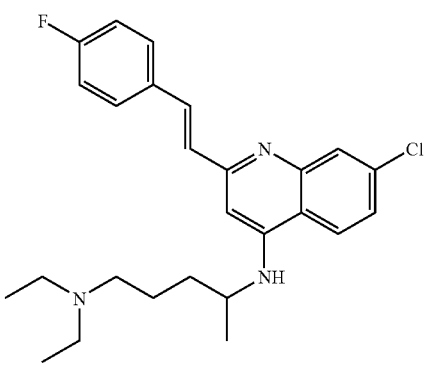

TABLE 1-continued
Exemplary anti-peripheral neuropathic compounds of the invention are shown in Tables 1 and 2 below:
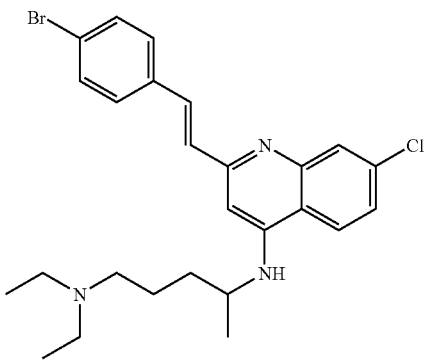
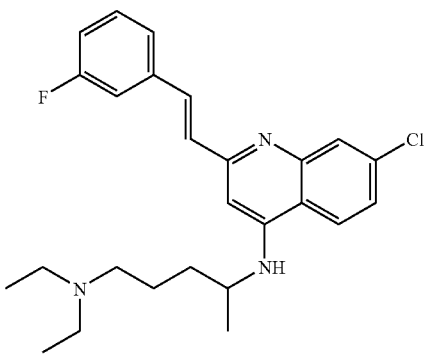
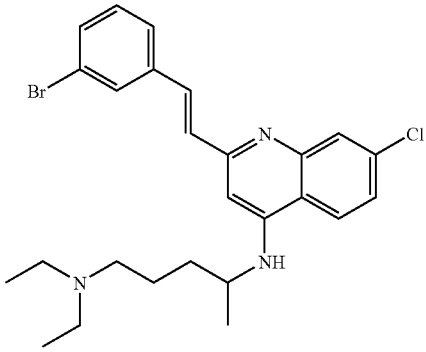
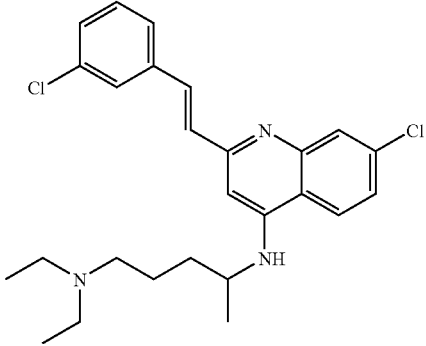
TABLE 2
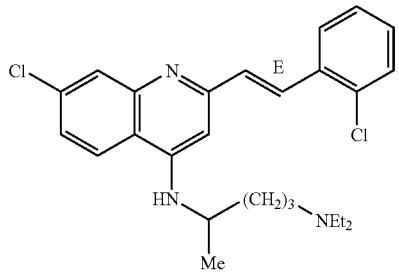
1,4-Pentanediamine, N4-[7-chloro-2-[(1E)-2-(2-chlorophenyl)ethenyl]-4-quinolinyl]-N1,N1-diethyl-
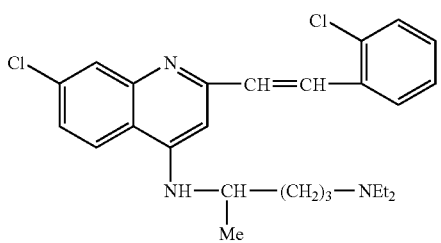
1,4-Pentanediamine, N4-[7-chloro-2-[2-(2-chlorophenyl)ethenyl]-4-quinolinyl]-N1,N1-diethyl-
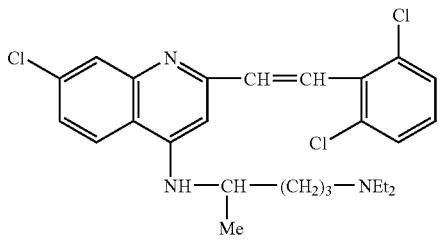
1,4-Pentanediamine, N4-[7-chloro-2-[2-(2,6-dichlorophenyl)ethenyl]-4-quinolinyl]-N1,N1-diethyl-
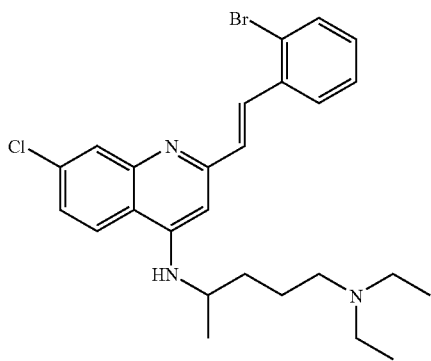

TABLE 2-continued
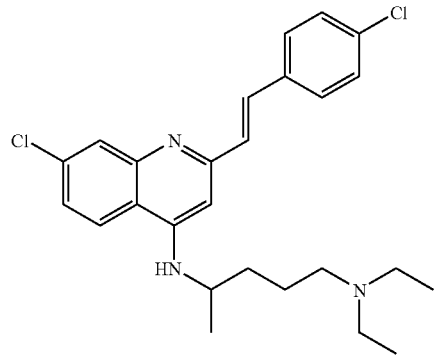
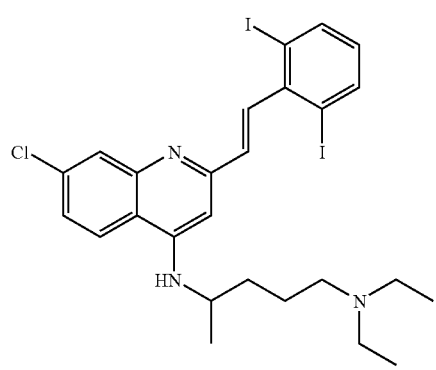
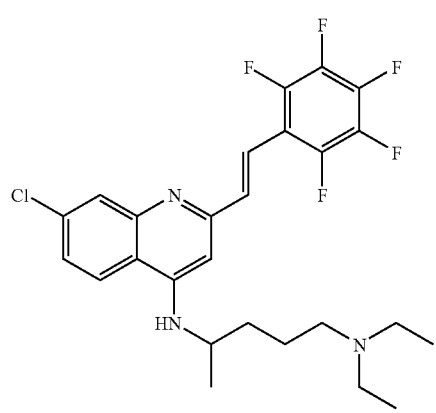
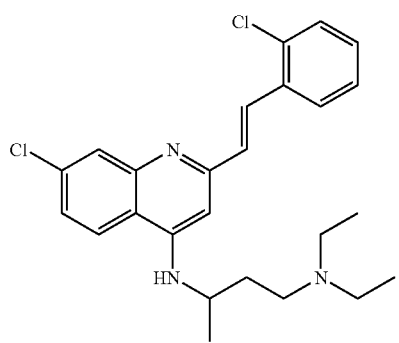
TABLE 2-continued
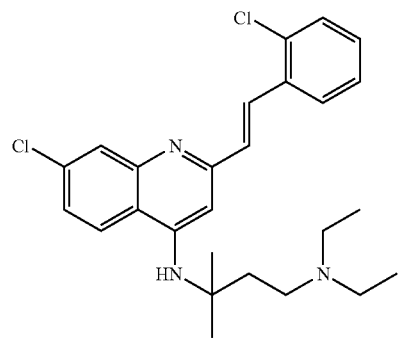
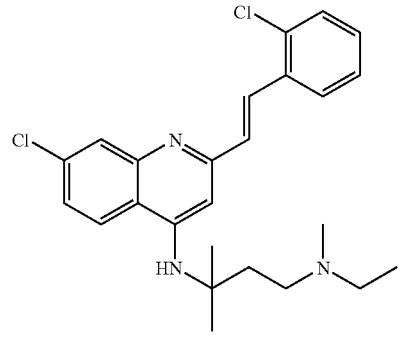
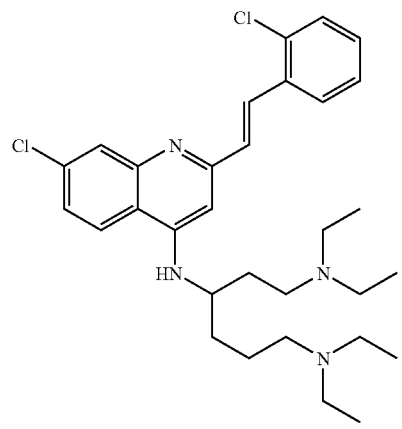
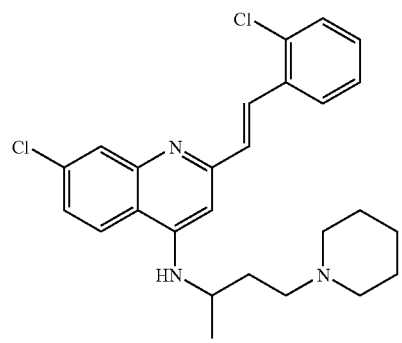

TABLE 2-continued

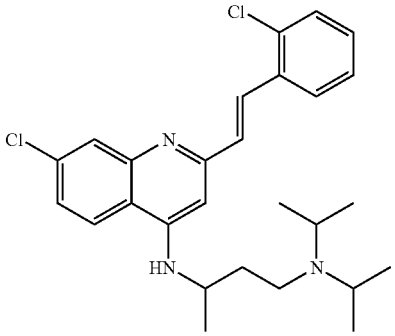

TABLE 3

7-chloro-4-(4-diethylamino-1-methylbutylamino)quinoline (chloroquine);
7-hydroxy-4-(4-diethylamino-1-methylbutylamino)quinoline; chloroquine phosphate;
7-chloro-4-(4-diethylamino-1-butylamino)quinoline (desmethylchloroquine);
7-hydroxy-4-(4-diethylamino-1-butylamino)quinoline;
7-chloro-4-(1-carboxy-4-diethylamino-1-butylamino)quinoline;
7-hydroxy-4-(1-carboxy-4-diethylamino-1-butylamino)quinoline;
7-chloro-4-(1-carboxy-4-diethylamino-1-methylbutylamino)quinoline;
7-hydroxy-4-(1-carboxy-4-diethylamino-1-methylbutylamino) quinoline;
7-chloro-4-(4-ethyl-(2-hydroxyethyl)-amino-1-methylbutylamino)quinoline (hydroxychloroquine);
7-hydroxy-4-(4-ethyl-(2-hydroxyethyl)-amino-1-methylbutylamino)quinoline; hydroxychloroquine phosphate;
7-chloro-4-(4-ethyl-(2-hydroxyethyl)-amino-1-butylamino)quinoline (desmethylhydroxychloroquine);
7-hydroxy-4-(4-ethyl-(2-hydroxyethyl)-amino-1-butylamino) quinoline;
7-chloro-4-(1-carboxy-4-ethyl-(2-hydroxyethyl)-amino-1-butylamino)quinoline;
7-hydroxy-4-(1-carboxy-4-ethyl-(2-hydroxyethyl)-amino-1-butylamino)quinoline;
7-chloro-4-(1-carboxy-4-ethyl-(2-hydroxyethyl)-amino-1-methylbutylamino)quinoline;
7-hydroxy-4-(1-carboxy-4-ethyl-(2-hydroxyethyl)-amino-1-methylbutylamino)quinoline;
8-[(4-aminopentyl)amino]-6-methoxydihydrochloride quinoline;
1-acetyl-1,2,3,4-tetrahydroquinoline; 8-[4-aminopentyl)amino]-6-methoxyquinoline dihydrochloride;
1-butyryl-1,2,3,4-tetrahydroquinoline;
7-chloro-2-(o-chlorostyryl)-4-[4-diethylamino-1-methylbutyl]aminoquiinoline phosphate;
3-chloro-4-(4-hydroxy-α,α'-bis(2-methyl-1-pyrrolidinyl)-2,5-xylidinoquinoline, 4-[(4-diethylamino)-1-methylbutyl]amino]-6-methoxyquinoline;
3,4-dihydro-1 (2H)-quinolinecarboxyaldehyde;
1,1'-pentamethylenediquinoleinium diiodide;
8-quinolinol sulfate;
Chloroquine 4-acetaminosalicylate;
Chlorquinaldol;
3-Methylchloroquine;
3-Carboxy-4-hydroxy-7-chloroquinoline;
4,7-Dichloroquinoline;
7-Chloro-4-hydroxyquinoline;
6-Chloroquinaldine;
N,2,6-Trichloro-4-benzoquinone imine;
Hydroxychloroquine;
Chloranil;
Clioquinol;
Cloxyquin;
Chloroquine sulfate;
8-Chloroquinoline;
4-Chloroquinoline;
3-Chloroquinoline;
6-Chloroquinoline;
2-Chloroquinoline;
2-Chloro-1,4-hydroxyquinone;
5-Chloroquinoline;
2-Chloro-1,4-benzoquinone;

TABLE 3-continued 2,6-Dichlorobenzoquinone;
Hydroxychloroquine sulfate;
Chloroxine;
7-Chloroquinolin-8-ol;
Chloroquinine phosphate;
2-Chloroquinoxaline;
Desethylchloroquine;
2,3-Dichloroquinoxaline-6-carbonylchloride;
2,3-Dichloroquinoxaline;
2-Chloroquinoline-4-carbonyl chloride;
4,11-Dichloroquinacridonequinone;
2,9-Dichloroquino(2,3-b)acridine-6,7,13,14(5H,12H)-tetrone;
2,3,6-Trichloroquinoxaline;
Chlorquinox;
Chloroquine hydrochloride;
Glafenine;
Chloroquine mustard;
N,N-Dideethylchloroquine;
Cletoquine;
Chloroquine-ethyl phenyl mustard;
4-Chloroquinazoline;
4-(3',5'-Bis(pyrrolidinomethyl)-4-hydroxyanilino)-7-chloroquinoline;
6-Chloroquinoxaline;
6-Chloro-8-aminoquinoline;
2-Chloromethyl-4-phenyl-6-chloroquinazoline-3-oxide;
2-Chloroquinazoline;
4-(2-Methyl-1-pyrrolidyl)-7-chloroquinoline;
6,7-Dichloroquinoline-5,8-dione;
6,7-Dichloroquinoxaline-2,3-dione;
Cloquinate;
8-Quinolinol, 7-bromo-5-chloro-;
Collagenan;
Dichlorquinazine;
4,7-Dichloroquinolinium tribromide;
Chloroquinoline;
Chloroquine diorotate;
2,4,6-Triamino-5-chloroquinazoline;
Methyl-8-(5,7-dichloroquinolyl)carbonic acid ester;
6-Amino-7-chloro-5,8-dioxoquinoline;
4,8-Dichloroquinoline;
5-Chloroquinolin-8-ol hydrochloride;
3-Phenyl-4-hydroxy-7-chloroquinolin-2(1H)-one;
N-Methyl-6-chloroquinolinium iodide;
3-Chloroquinuclidine hydrochloride;
Halacrinate;
1-Phenacyloxime-4,5-dichloroquinolinium chloride hydrate;
Chloroquine diascorbate;
2-(7-Chloroquinolin-4-yl)anthranilic acid hydrochloride;
Tripiperaquine;
2-(2-Chlorostyryl)-4-(delta-diethylamino-alpha-methylbutylamino)-7-chloroquinazoline;
(+)-Chloroquine;
(−)-Chloroquine;
7-Chloro-4-(3-octylaminopropyl)aminoquinoline 1-oxide;
Ethyl chloroquine mustard;
L-Chloroquine;
2,6-Dianilino-6-chloroquinoxaline;
2-(2-(5-Nitrofuryl)vinyl)-4-(delta-diethylamino-alpha-methylbutylamino)-7-chloroquinazoline;
D-Chloroquine;
2,3-Bis(allylamino)-6-chloroquinoxaline;
7-Chloroquinolin-4-ol hydrochloride;
2-Amino-3,4-dichloroquinoline;
Quizalofop;
Presocyl;
Tris(5,7-dichloroquinolin-8-olato-N1,O8)aluminium;
Contramibial;
Quinclorac;
N-(4-((7-Chloroquinolin-4-yl)amino)pentyl)-N-ethylacetamide;
7-Bromo-5-chloroquinolin-ol;
Chlorsulfaquinoxaline;
1-Dimethylaminopropyl-3-methyl-6-chloroquinoxaline-2(1H)-one;
Propaquizafop;
3-Chloroquinoline-8-carboxylic acid;
5,10,15,20-Tetraphenyl-1-3-(4-(4-aminobutyl)-7-chloroquinoline)propioamidoporphine;
4-((Carboxymethyl)amino)-5,7-dichloroquinoline-2-carboxylic acid;
4-((Carboxymethyl)oxy)-5,7-dichloroquinoline-2-carboxylic acid;
5,7-Dichlorokynurenic acid;

TABLE 3-continued

N1,N2-Bis(7-chloroquinolin-4-yl)cyclohexane-1,2-diamine;
Meclinertant;
5-(2-(1-(3-(2-(7-Chloroquinolin-2-yl)ethenyl)benzyl)indol-7-yl)ethyl)-
1H-tetrazole;
(N1-(7-Chloroquinolin-4-yl)-3-(N3,N3-diethylamino)propylamine)
dihydrochloride trihydrate; and
enantiomers thereof, and mixtures thereof, and suitable pharmaceutical
salts thereof.

Another aspect of the invention is directed toward methods of treating or preventing neuropathy in a subject including administering to the subject a modulator of glial cell-derived neurotrophic factor (GDNF) receptor.

In certain embodiments, the modulator may be an agonist of the GDNF receptor GFRα1 and/or GFRα2. The agonist may be a non-peptidyl agonist, particularly is XIB4035.

A further aspect of the present invention is directed toward topical lotions including a subject anti-peripheral neuropathic quinoline compound, or a pharmaceutically acceptable salt thereof; and a pharmaceutically acceptable carrier formulated for topical application.

In another aspect, the present invention provides "pharmaceutically acceptable" compositions, that include a therapeutically effective amount of one or more of the compounds described herein, formulated together with one or more pharmaceutically acceptable carriers (additives) and/or diluents. The pharmaceutical compositions of the present invention may be specially formulated for administration in solid or liquid form, including those adapted for topical application, for example, as a cream, ointment, drops, gels, or a controlled-release patch or spray or sustained-release formulation applied to the skin, for example, as a cream or foam.

Certain aspects of the invention include topical lotion formulations. A topical lotion comprises a therapeutically effective amount of one or more of the compounds described herein and a topical carrier. Topical carriers include but are not limited to creams, ointments, drops, gels, or a controlled-release patch or spray or sustained-release formulation applied to the skin. Suitable carrier components include, but are not limited to, mineral oil, sorbitan monostearate, polysorbate 60, cetyl esters wax, cetearyl alcohol, 2-octyl-dodecanol, benzyl alcohol, liquid petroleum, white petroleum, propylene glycol, polyoxyethylene polyoxypropylene compound, emulsifying wax and water.

The phrase "pharmaceutically acceptable" is employed herein to refer to those materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject extract from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; sterile distilled water; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, and perfuming agents, preservatives and antioxidants can also be present in the compositions.

The compounds of the present invention can be administered orally, parenterally, for example, subcutaneously, intravenously, intramuscularly, intraperitoneally, by intranasal instillation, by inhalation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The compounds of the present invention may also be administered directly to the airways in the form of a dry powder. For use as a dry powder, the compounds of the present invention may be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume. For inhalation, the system has a plurality of chambers or blisters each containing a single dose of the pharmaceutical composition and a select element for releasing a single dose.

Suitable powder compositions include, by way of illustration, powdered preparations of the active ingredients thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants, and co-solvents and may be filled into conventional aerosol containers that are closed by a suitable metering valve.

EXAMPLES

First we used a transgenic mouse line (GFAP-DN-erbB4) in which erbB receptor function in non-myelinating cells (NMSCs) is eliminated by expression of a dominant negative erbB receptor (6). Around 21 days of age, these mice begin to show symptoms of SFN, including loss of thermal nociception, breakdown of Remak bundles (unmyelinated axons surrounded by a NMSC), degeneration of c-fibers and death of NMSCs. This degenerative process coincides with dramatic reduction in the levels of GDNF expression in peripheral nerves, suggesting that loss of GDNF could be implicated in the pathogenesis of SFN (6) in this model.

As a first test of the effects of target-derived trophic support via GDNF receptor activation in this model we crossed GFAP-DN-erbB4 mice with a previously characterized mouse line that over-expresses GDNF in the skin under the control of the keratin 14 promoter (K14-GDNF) (8). In these mice GDNF expression in the skin is ~6-fold higher than that found in wild type skin and leads to increased numbers of sensory terminals (8), indicating that the transgenic GDNF is active and has an impact on sensory neurons. Importantly, despite this hyper-innervation, K14-GDNF mice have normal sensory behavior and are otherwise normal (8), indicating that GDNF over-expression in the skin has no deleterious effects.

GFAP-DN-erbB4 and K14-GDNF double and single transgenic mice were tested for sensory function using a hot plate test. As shown previously, adult (6-week-old) K14-GDNF mice responded normally in this assay (8) while GFAP-DN-erbB4 mice had a dramatic loss in thermal-nociception and needed to be removed from the hot plate after 30 seconds (6). In contrast, withdrawal latencies in GFAP-DN-erbB4::K14-GDNF double transgenic mice were indistinguishable from those of wild types, indicating that the sensory deficit in GFAP-DN-erbB4 mice was rescued by over-expression of GDNF in the skin.

In our previous characterization of GFAP-DN-erbB4 mice we showed that loss of thermal nociception correlates with dramatic alterations in peripheral nerve structure, including disruption of Remak bundles (6). Therefore, we used electron microscopy to examine Remak bundle structure in mice of the four genotypes. Remarkably, GFAP-DN-erbB4::K14-GDNF double transgenic mice contained many normal-appearing Remak bundles. Since the ability of mice to respond to noxious thermal stimuli depends on c-fiber sensory terminals in the footpads and patients with symptomatic SFN have reduced epidermal nerve fiber density (10), we tested whether these terminals were disrupted in GFAP-DN-erbB4 mice, and if so, can they be rescued by GDNF over-expression. Quantification of free nerve endings identified by expression of the neuronal marker protein gene product 9.5 (PGP9.5) at P30 confirmed previous reports of hyper-innervation in the skin of K14-GDNF mice compared to wild type skin (8), while GFAP-DN-erbB4 mice showed reduced nerve terminals in the skin at this age. Consistent with the rescue of thermal nociception in double transgenic mice, we observed preservation of nerve terminals in the skin of GFAP-DN-erbB4::K14-GDNF mice compared to GFAP-DN-erbB4 mice. Over-expression of GDNF not only improved the axonal phenotyes of GFAP-DN-erbB4 mice but also reduced the extent of Schwann cell death, indicating that trophic support delivered at the target of innervation preserves the health of glial cells along the nerve. Importantly, levels of DN-erbB4 expression in sciatic nerves of double transgenic mice were similar to those in GFAP-DN-erbB4 mice, indicating that reversion of the SFN in double transgenic mice was not due to an effect of GDNF on DN-erbB4 expression. These results show that GDNF over-expression in the skin also rescues the anatomical phenotypes along the nerve produced by DN-erbB4 expression in NMSCs.

The results described above suggest that GDNF over-expression in the skin could be used to treat progressive SFNs like the one found in GFAP-DN-erbB4 mice. However, since K14-GDNF mice overexpress this factor from embryonic development, the possibility that alterations in development could have contributed to the phenotypic rescue could not be overlooked. Furthermore, when considering treatment of humans, GDNF over-expression would require some type of gene therapy, which has its own drawbacks and complications. Thus, we felt it was necessary to test alternative approaches to activate GDNF signaling in the skin as a treatment for SFN. Since proteins such as GDNF do not readily diffuse through the skin, we tested if XIB4035, a non-peptidyl small molecule agonist for the GDNF receptor GFRα1 (11) would be a useful alternative. XIB4035 had previously been shown to activate the Ret co-receptor by binding to the GFR□1 GDNF receptor in both human and murine cells (11).

We generated a cream containing XIB4035 (1.2 mM) and applied it directly to the hind paws of GFAP-DN-erbB4 and wild type mice twice daily for a period of 4 weeks starting at the time of weaning (P21). Importantly, by this age GFAP-DN-erbB4 mice already exhibit neuropathic symptoms (6). Thus, these experiments would test whether activation of Ret signaling has therapeutic effects after disease onset. To control for potential effects of the control cream, mice of both genotypes were treated in the same way with the base cream without the drug. Mice were tested for responses to noxious thermal stimulus prior to the initiation of treatment and every 7 days throughout the treatment period. Over the 4 week treatment period, the behavior of wild type mice remained normal, independent of the presence of XIB4035 in the cream while GFAP-DN-erbB4 mice treated with control cream progressively lost thermal nociception as we found in untreated animals (6). In contrast, when treated with cream containing XIB4035, GFAP-DN-erbB4 mice showed dramatic preservation of thermal nociception, their behavior being similar to that of wild type mice. As expected from our previous characterization of GFAP-DN-erbB4 mice (6), response thresholds to punctate mechanical stimuli remained normal in all groups after the 4 weeks of treatment, indicating that the drug had no effect on mechanoreception. Together, these findings indicate that topical treatment with XIB4035 preserves the ability of mice with SFN to respond to noxious heat stimulus without inducing hypersensitivity. They also show that treatment of unaffected mice with XIB4035 had no deleterious effects on their ability to respond to heat or mechanical stimuli.

From the anatomical point of view, similarly to what we found in the double transgenic mice, 4-week treatment with XIB4035 prevented the degeneration of Remak bundles and c-fiber axons. Morphometric analysis showed that XIB4035 treatment preserved both the size of c-fiber axons and the number of c-fibers per Remak bundle in GFAP-DN-erbB4 mice. Furthermore, NMSC apoptosis was also significantly reduced in GFAP-DN-erbB4 mice treated with XIB4035. Interestingly, like GDNF over-expression, drug treatment not only prevented degeneration of sensory nerve terminals in the footpad skin of GFAP-DN-erbB4 mice, but it increased the density of nerve terminals in wild type skin.

As it is unlikely that SFN is always caused by glial dysfunction, we considered it necessary to test the effectiveness of XIB4035 treatment on SFN resulting from a different pathogenic mechanism. Therefore we tested the efficacy of our therapeutic approach in resiniferatoxin (RTX)-induced SFN (9). RTX-induced SFN involves intraperitoneal injection of an ultrapotent capsaicin analog that targets c-fiber terminals by binding to and activating TRPV1 channels resulting in calcium influx, which induces loss of skin innervation and loss of thermal nociception (9). After RTX injection, mice were either treated immediately with XIB4035 or treatment was delayed by 12 hours. Both treatment paradigms yielded similar results.

Similar to the effect seen in GFAP-DN-erbB4 mice, treatment with XIB4035 greatly improved thermal nociception in the RTX model. Seven days after RTX treatment paw withdrawal latencies were greatly increased in animals treated with control cream. In contrast, RTX-injected animals that were treated with XIB4035 had remarkable preservation of their ability to respond to noxious heat. Furthermore, innervation of the skin was preserved as a result of XIB4035 treatment in RTX-injected mice. As expected based on the preservation of thermal nociception and skin innervation, Remak bundle structure was also significantly improved in RTX-injected animals treated with XIB4035. Both c-fiber area and the number of fibers per Remak bundle were improved by treatment with XIB4035 in RTX-induced SFN.

Together, these results indicate that SFNs may be treated by supplying ligands for neurotrophic factor receptors at the target of innervation, providing an alternative to invasive or systemic routes of delivery. Using either "gene therapy" or a "topical" pharmacological approach we show that application of GDNF receptor ligands to the skin results in preservation of nerve structure and function in two mouse models of SFN. Since SFN occurs frequently as a late-onset complication of a number of diseases, e.g. diabetes, topical application of GDNF receptor ligands can be considered as a preventive therapy after the first disease symptoms, e.g. hyperglycemia, appear. Nevertheless, since topical application of the drug to mice was effective after the onset of sensory defects, our studies indicate that this type of treatment could help even after patients develop SFN symptoms.

The results presented herein together with our previous analysis of GFAP-DN-erbB4 mice (6) also provide insights into the roles of trophic factors in adult nerves. The emerging picture is that GDNF produced by Schwann cells along the nerve is necessary for the maintenance of c-fiber structure and function, and that endogenous GDNF can be replaced by application of GDNF or synthetic ligands to the sensory nerve endings. If similar mechanisms are at work in other nerves, this type of therapeutic intervention could be used to treat other neuropathies, including those involving central nerves, i.e. optic nerve. Furthermore, the use of this type of drug to treat degenerative processes involving other neurons that express receptors for the GDNF family, e.g. spinal cord motorneurons, using intramuscular injections, should be considered. Furthermore, these results demonstrate that tyrosine kinase signaling in cells or cell segments within the skin can be modified by the topical application of a non-peptidyl molecule. Therefore, in addition to the results presented herein, this strategy might also be useful to locally treat other disorders such as skin cancer (12, 13).

Previous animal tests of the effectiveness of systemic or intrathecal injection of neurotrophic factors as therapeutic agents for peripheral neuropathy have provided encouraging results (14-16). However, human trials using injections of trophic factors to treat peripheral neuropathies have either resulted in severe side effects or have been ineffective altogether. For example, trials examining the efficacy of NGF treatment in diabetic patients with peripheral neuropathy or patients with HIV neuropathy have shown some improvement in the patient's perception of symptom severity, but side effects including myalgia, peripheral edema, and hyperalgesia were also observed (17-19). Test of GDNF injections for other neurological disorders have been marred by serious side effects. For example, intracerebroventricular administration of GDNF results in weight loss, anorexia, and nausea while providing little benefit to Parkinson's disease patients (20). Our results indicate that topical treatment with small molecule agonists for neurotrophic factor receptors, e.g. GDNF receptor ligands, can provide an effective treatment for peripheral neuropathies without the side effects associated with generalized delivery.

Animals and induction of neuropathy using RTX. Transgenic mouse lines used were as previously described (6, 8). Animals were kept in the animal facility with free access to food and water. Behavioral experiments were performed in a quiet environment at the same time of day. The hot plate test was performed using a "controlled hot-plate analgesia meter" (Columbus Instruments) heated to 55° C. Paw withdrawal latency was measured as the time required for the mouse to visibly respond to the thermal stimulus, e.g. licking paws, lifting paws, or jumping off of the plate. Mechanical sensitivity was tested by simulation of the plantar surface of the hind paw with a series of von Frey filaments while the animal was placed on an elevated wire grid. The threshold was determined as the lowest force that evoked a visible withdrawal response. 8-week-old ICR mice weighing at least 30 g were injected intraperitoneally with RTX (50 mg/kg) or vehicle (10% Tween-80, 10% ethanol in isotonic saline) (9).

Preparation and Use of XIB4035. The cream containing XIB4035 (1.2 mM, Matrix Scientific, Columbia, S.C.) consisted of N-methyl-pyrrolidone (5%), isopropyl myristate (5%) and petroleum jelly (90%). Control cream had the same ingredients without XIB4035. Cream was applied twice daily to the hind paws of isoflurane anesthetized mice starting at P21 for a period of 9 days (for analysis of cell death in sciatic nerves) or 4 weeks (all other studies using GFAP-DN-erbB4). Treatment of RTX-induced neuropathy began at the time of RTX injection or 12 hours after RTX injection and proceeded twice daily for a period of one week.

Plastic Embedding and Electron Microscopy. Tissue was prepared as in (6). Briefly, mice were perfused intracardially with 2% paraformaldehyde, 2.5% gluteraldehyde and 0.03% picric acid in 0.1 M cacodylate buffer (pH 7.2). Tissue was post-fixed overnight at 4° C. and embedded in Epon. Ultrathin sections were cut, collected on cellodin-coated grids and stained using uranyl acetate and lead citrate. Photographs were taken using the Tecnai $G^2$ Spirit BioTWIN transmission electron microscope.

Immunohistochemistry. Mice were anesthetized with 2.5% Avertin and footpad skin was removed and immersion fixed in 4% paraformaldehyde, 14% picric acid in 0.1 M phosphate buffer (pH 7.3) overnight at 4° C. and cryoprotected in 20% sucrose overnight at 4° C. Tissues were embedded in OCT and sectioned at 30 □m and stained as floating sections by washing 3 times for 5 minutes in PBS+0.1% Triton-X 100, blocked for 30 minutes in PBS+0.1% Triton-X 100+10% normal goat serum and then incubated, PGP9.5 rabbit polyclonal antibody (Ultraclone, 1:1000), overnight at 4° C. Sections were washed 3 times for 10 minutes in PBS+ 0.1% Triton-X 100 then incubated in donkey anti-rabbit Alexa-488 (Invitrogen) 1:300 for 2 hours at room temperature. Nuclei were stained with DAPI and sections were mounted with Gel-Mount.

Cell Death Detection. Sciatic nerves were dissected from mice perfused with 4% paraformaldehyde in PBS and fixed overnight at 4° C. Nerves were embedded in OCT and 16 □m thick transverse sections were processed for TUNEL as follows. Sections were washed 3 times for 5 minutes with PBS followed by proteinase K digestion (0.02 U/mL) in 10 mM TRIS/HCl pH 7.5 for 30 minutes at 37° C. Digested sections were fixed with 4% paraformaldehyde at room temperature for 20 minutes followed by 3 washes in PBS for 5 minutes. Apoptotic nuclei were identified using the In Situ Cell Death Detection Kit (Roche). Nuclei were stained with DAPI and sections were mounted with Gel-Mount.

REFERENCES

1. N. R. Holland et al., *Ann Neurol* 44, 47 (July 1998).
2. D. Lacomis, *Muscle Nerve* 26, 173 (August 2002).
3. D. R. Comblath, A. Hoke, *Curr Opin Neurol* 19, 446 (October 2006).
4. W. Luo et al., *Neuron* 54, 739 (June 7, 2007).
5. D. C. Molliver et al., *Neuron* 19, 849 (October 1997).
6. S. Chen et al., *Nat Neurosci* 6, 1186 (November 2003).
7. R. Hellweg, G. Raivich, H. D. Hartung, C. Hock, G. W. Kreutzberg, *Exp Neurol* 130, 24 (November 1994).
8. M. Zwick et al., *J Neurosci* 22, 4057 (May 15, 2002).
9. Y. L. Hsieh, H. Chiang, T. J. Tseng, S. T. Hsieh, *J Neuropathol Exp Neurol* 67, 93 (February 2008).
10. N. R. Holland et al., *Neurology* 48, 708 (March 1997).
11. K. Tokugawa et al., *Neurochem Int* 42, 81 (January 2003).
12. D. J. Easty, D. C. Bennett, *Melanoma Res* 10, 401 (October 2000).
13. F. J. Lejeune, D. Rimoldi, D. Speiser, *Expert Rev Anticancer Ther* 7, 701 (May, 2007).
14. D. L. Bennett et al., *J Neurosci* 18, 3059 (Apr. 15, 1998).
15. D. Perrelet et al., *Nat Cell Biol* 4, 175 (February 2002).
16. Q. Yan, J. Wang, C. R. Matheson, J. L. Urich, *J Neurobiol* 38, 382 (Feb. 15, 1999).
17. S. C. Apfel et al., *Neurology* 51, 695 (September 1998).
18. J. C. McArthur et al., *Neurology* 54, 1080 (Mar. 14, 2000).
19. G. Schifitto et al., *Neurology* 57, 1313 (Oct. 9, 2001).
20. J. G. Nutt et al., *Neurology* 60, 69 (Jan. 14, 2003).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. All references cited herein, and references cited therein are incorporated by reference as if each was specifically and individually indicated to be incorporated by reference.

What is claimed:

1. A method of treating a small fiber peripheral neuropathy in a subject determined to be in need thereof comprising:
    topically administering to the subject an anti- peripheral neuropathic quinoline compound of the formula:

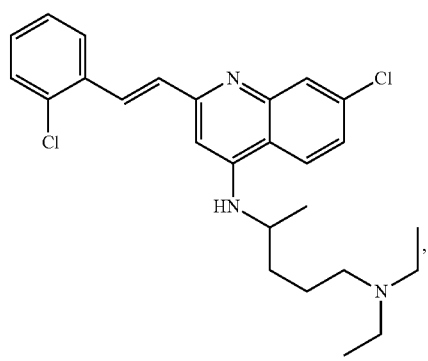

or a pharmaceutically acceptable salt thereof.

2. The method of claim 1, wherein the subject is human.

3. The method of claim 1, wherein compound is administered in a lotion at 1.2 mM, and the lotion further comprises N-methyl-pyrrolidone (5%), isopropyl myristate (5%) and petroleum jelly (90%).

4. The method of claim 1 further comprising the antecedent step determining that the subject is in need of said method by detecting the small fiber neuropathy in the subject.

5. The method of claim 1 further comprising the subsequent step of detecting a resultant diminution of the small fiber neuropathy.

6. The method of claim 1 further comprising the antecedent step determining that the subject is in need of said method by detecting the small fiber neuropathy in the subject, and the subsequent step of detecting a resultant diminution of the small fiber neuropathy.

7. A method of treating a small fiber peripheral neuropathy in a subject determined to be in need thereof comprising:
topically administering to the subject an agonist of glial cell-derived neurotrophic factor (GDNF) receptor GFRα1 or GFRα2, under conditions effective to treat the peripheral neuropathy in the subject, wherein the agonist is N4-{7-chloro-2-[(E)-2-(2-chloro-phenyl)-vinyl]-quinolin-4-yl}-N1, N1-diethyl-pentane-1,4-diamine (XIB4035).

8. The method of claim 7, wherein the subject is human.

9. The method of claim 7, wherein compound is administered in a lotion at 1.2 mM, and the lotion further comprises N-methyl-pyrrolidone (5%), isopropyl myristate (5%) and petroleum jelly (90%).

10. The method of claim 7 further comprising the antecedent step determining that the subject is in need of said method by detecting the small fiber neuropathy in the subject, and the subsequent step of detecting a resultant diminution of the small fiber neuropathy.

11. A topical lotion comprising an anti-peripheral neuropathic effective amount of an anti-peripheral neuropathic quinoline compound N4-{7-chloro-2-[(E)-2-(2-chloro-phenyl)-vinyl]-quinolin-4-yl}-N1, N1-diethyl-pentane-1,4-diamine(XIB4035), or a pharmaceutically acceptable salt thereof, and a pharmaceutically acceptable carrier formulated for topical application.

12. The lotion of claim 11 containing the compound at 1.2 mM, and further comprising N-methyl-pyrrolidone (5%), isopropyl myristate (5%) and petroleum jelly (90%).

* * * * *